United States Patent
Furukawa et al.

(10) Patent No.: US 11,026,320 B1
(45) Date of Patent: Jun. 1, 2021

(54) CHARGED PARTICLE IRRADIATION APPARATUS

(71) Applicant: B dot Medical Inc., Tokyo (JP)

(72) Inventors: Takuji Furukawa, Tokyo (JP); Yousuke Hara, Tokyo (JP)

(73) Assignee: B DOT MEDICAL INC., Tokyo (JP)

( * ) Notice: Subject to any disclaimer, the term of this patent is extended or adjusted under 35 U.S.C. 154(b) by 0 days.

(21) Appl. No.: 17/170,208

(22) Filed: Feb. 8, 2021

(30) Foreign Application Priority Data

Mar. 26, 2020 (JP) .............................. JP2020-055716

(51) Int. Cl.
*H05H 7/04* (2006.01)
*G21K 1/06* (2006.01)
*A61N 5/10* (2006.01)

(52) U.S. Cl.
CPC ............. *H05H 7/04* (2013.01); *A61N 5/1078* (2013.01); *G21K 1/065* (2013.01); *A61N 2005/1087* (2013.01); *H05H 2007/043* (2013.01); *H05H 2007/045* (2013.01)

(58) Field of Classification Search
CPC .......... A61N 2005/1087; A61N 5/1043; A61N 5/1077; A61N 5/1081; A61N 5/1078; A61N 2005/1052; A61N 2005/1055; A61N 2005/1058; A61N 2005/1061; A61N 2005/1063; A61N 2005/1074; A61N 2005/1076; A61N 2005/1089; A61N 2005/1091; A61N 2005/1095; A61N 2005/1096; A61N 2005/1098; A61N 5/10; A61N 5/1039; A61N 5/1045; H05H 7/04;

(Continued)

(56) References Cited

U.S. PATENT DOCUMENTS

| 4,660,465 | A | 4/1987 | Jentzsch et al. |
| 10,431,418 | B1 * | 10/2019 | Mizushima ............ H01J 37/141 |
| 10,912,954 | B2 * | 2/2021 | Hara .................... A61N 5/1045 |

(Continued)

FOREIGN PATENT DOCUMENTS

| JP | 2018-38670 A | 3/2018 |
| JP | 6387476 B1 | 9/2018 |
| JP | 2019-180654 A | 10/2019 |

OTHER PUBLICATIONS

Decision to Grant a Patent for JP2020-055716 dated Aug. 28, 2020.

*Primary Examiner* — David A Vanore
(74) *Attorney, Agent, or Firm* — Birch, Stewart, Kolasch & Birch, LLP (57) ABSTRACT

The invention provides a charged particle irradiation apparatus including: a focusing magnet that deflects a charged particle beam to continuously change an irradiation angle of the beam to an isocenter; an irradiation nozzle that continuously moves along a shape on an exit side of an effective magnetic field region of the focusing magnet, wherein the beam exiting the focusing magnet is emitted to the isocenter through the irradiation nozzle; a power supply rail along the shape on the exit side of the region; and a collector shoe fixed to the irradiation nozzle and configured to slide along the rail to supply power from the rail to the irradiation nozzle. A surface of the collector shoe contacted with the rail has the same bend radius as or average bend radius of the rail, and/or the collector shoe slides along the rail in contact with a flat side surface of the rail.

8 Claims, 10 Drawing Sheets

(58) Field of Classification Search
CPC ....... H05H 2007/043; H05H 2007/045; G21K 1/065
USPC ................... 250/492.1, 393; 235/375, 380
See application file for complete search history.

(56) References Cited

U.S. PATENT DOCUMENTS

| | | | | |
|---|---|---|---|---|
| 2002/0030164 | A1* | 3/2002 | Akiyama | G21K 5/04 250/492.1 |
| 2011/0125524 | A1* | 5/2011 | Tenarvitz | G07C 9/257 705/3 |
| 2012/0305790 | A1* | 12/2012 | Hanawa | A61N 5/1043 250/393 |
| 2016/0193482 | A1* | 7/2016 | Fahrig | A61N 5/1067 600/1 |
| 2017/0229281 | A1* | 8/2017 | Furukawa | G21K 1/093 |
| 2018/0064958 | A1 | 3/2018 | Kobayashi et al. | |

* cited by examiner

FIG. 7A — SHAPE OF CONTACT SURFACE 123a WITH LARGE CONTACT RESISTANCE

FIG. 7B — SHAPE OF CONTACT SURFACE 123a WITH SMALL CONTACT RESISTANCE

CHARGED PARTICLE IRRADIATION APPARATUS

BACKGROUND OF THE INVENTION

Field of the Invention

The present invention relates to a charged particle irradiation apparatus.

Description of the Related Art

Conventionally, particle therapy treatment to irradiate a malignant tumor such as a cancer with a charged particle beam accelerated by high energy and treat the malignant tumor has been employed.

In particle therapy treatment, a scanning irradiation method for scanning a side direction with a thin charged particle beam extracted from an accelerator by using a scanning magnet, further, dividing a lesion into respective layers in the beam traveling direction, and enabling three-dimensional irradiation has been employed. To transport the charged particle beam extracted from the charged particle accelerator to an irradiation target inside a treatment room, a beam transport system including a bending magnet, a focusing magnet, or the like is used, and the beam transport system has an irradiation nozzle having a scan magnet or an energy modulation unit at the terminal end on the irradiation target side.

In a particle beam irradiation apparatus disclosed in Japanese Patent Application Laid-Open No. 2013-505757, while an irradiation angle can be selected continuously with respect to an irradiation target, a rotating gantry used for rotating a huge irradiation apparatus is required. Herein, a large amount of current is required to be supplied to apparatuses such as electromagnets, an irradiation apparatus, and the like used for particle therapy treatment, and power cables such as a CV cable having a large current tolerance (cross-linked polyethylene insulating vinyl sheathed cable) are used. Such a cable is relatively thick cable, and such a thick cable has a large bend radius (curvature). When several tens to several hundreds of these thick cables are bundled and used, there is a problem of an increased storage space for the cables. Further, since a rotating gantry rotates by the maximum of around 180 degrees clockwise or anticlockwise, cables are required to be rotated together, and there is a problem of tangling or damage such as friction between the cables due to rotation.

Japanese Patent No. 6387476 discloses a charged particle irradiation apparatus that irradiates a target with a charged particle beam from any angle without using a rotating gantry.

Figure 10:
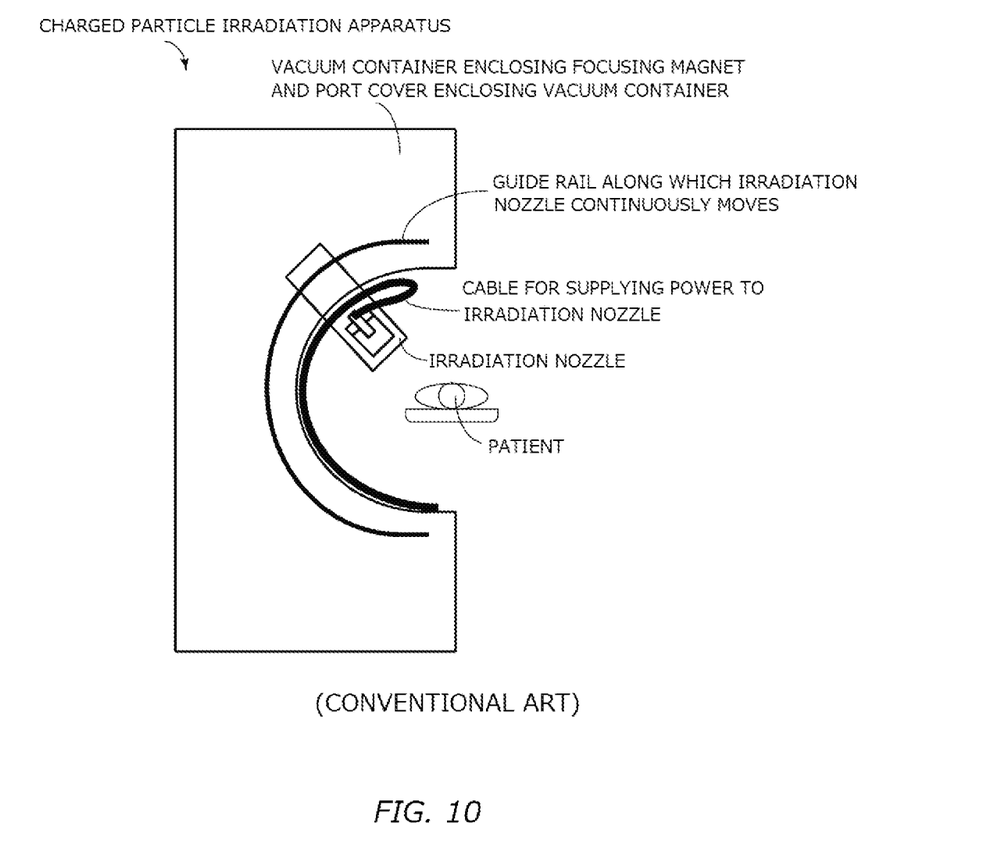
FIG. 10 is a diagram illustrating a charged particle irradiation apparatus of a conventional art.

In a conventional charged particle irradiation apparatus, when an irradiation nozzle and the like supplied with a large amount of current are configured to move, a cabtyre cable or the like that can move while current is being conducted are used in general as illustrated in FIG. 10. However, since a cable such as a cabtyre cable has a significantly thick sheath portion, a large bend radius is needed, and this leads to a problem of a huge apparatus as a whole. Further, when such large and thick cables are located at a position in a sight of a patient and the moving cables can be seen by the patient under treatment, this may give the patient mental pressure or anxiety.

SUMMARY OF THE INVENTION

In view of the above, the present invention intends to provide a charged particle irradiation apparatus configured such that power is supplied from a power supply rail to an irradiation nozzle without using a relatively thick power supply cable used for operating the irradiation nozzle.

The present invention includes the following aspects [1] to [8]:

[1] A charged particle irradiation apparatus including:
a focusing magnet that deflects a charged particle beam to continuously change an irradiation angle of the charged particle beam to an isocenter;
an irradiation nozzle that continuously moves along a shape on an exit side of an effective magnetic field region of the focusing magnet, wherein a charged particle beam exiting the focusing magnet is emitted to the isocenter through the irradiation nozzle;
a power supply rail provided so as to extend along the shape on the exit side of the effective magnetic field region; and
a collector shoe fixed to the irradiation nozzle via a support member and configured to slide along the power supply rail to supply power from the power supply rail to the irradiation nozzle,
wherein a surface of the collector shoe contacted with the power supply rail has the same bend radius as the power supply rail or an average bend radius of the power supply rail, and/or
wherein the collector shoe slides along the power supply rail while being in contact with a flat side surface of the power supply rail.

[2] The charged particle irradiation apparatus according to [1], wherein while the focusing magnet, the power supply rail, and the collector shoe are enclosed in a port cover, a whole or a part of the irradiation nozzle is located outside the port cover.

[3] A charged particle irradiation apparatus including:
a focusing magnet that deflects a charged particle beam to continuously change an irradiation angle of the charged particle beam to an isocenter;
an irradiation nozzle that continuously moves along the shape on the exit side of an effective magnetic field region of the focusing magnet, wherein a charged particle beam exiting the focusing magnet is emitted to the isocenter through the irradiation nozzle;
a power supply rail provided so as to extend along a shape on an exit side of the effective magnetic field region; and
a collector shoe fixed to the irradiation nozzle via a support member and configured to slide along the power supply rail to supply power from the power supply rail to the irradiation nozzle,
wherein the collector shoe is formed of a plurality of collector portions, and
wherein a surface of each of the collector portions that is contacted with the power supply rail has the same bend radius as the power supply rail or an average bend radius of the power supply rail.

[4] The charged particle irradiation apparatus according to any one of [1] to [3], wherein biasing means are provided between the support member and the collector shoe, and a constant weight is applied on the collector shoe by the biasing means.

[5] The charged particle irradiation apparatus according to any one of [1] to [4] further including:
a guide rail provided so as to extend along the shape on the exit side of the effective magnetic field region; and
a drive unit fixed to the irradiation nozzle via the support member and configured to continuously move along the guide rail while the irradiation nozzle is supported by the guide rail, wherein power is supplied from the power supply rail to the drive unit via the collector shoe.

[6] The charged particle irradiation apparatus according to any one of [1] to [5], wherein the focusing magnet has a coil pair arranged so as to interpose a path of a charged particle beam, wherein the coil pair is configured to generate an effective magnetic field region whose magnetic field is oriented to a direction (Z-axis) orthogonal to a traveling direction (X-axis) of a charged particle beam in response to input of current, where an axis orthogonal to both the X-axis and the Z-axis is defined as a Y-axis, wherein on the XY plane, a charged particle beam deflected at a deflection angle $\phi$ relative to the X-axis at a deflection point Q and entering the effective magnetic field region is deflected by the effective magnetic field region and is emitted to the isocenter at an irradiation angle $\theta$ relative to the X-axis through the irradiation nozzle, an arbitrary point P2 on a boundary defining the effective magnetic field region and located on an exit side of a charged particle beam is located at an equal distance $r_1$ from the isocenter, the point P2 and a point P1 on a boundary defining the effective magnetic field region and located on an incident side of a charged particle beam are on an arc of a circle of a radius $r_2$ and a central angle $(\theta+\phi)$, and a distance R between the deflection point Q and the point P1 satisfies relational Equation (4), where a distance between the deflection point Q and the isocenter is denoted as L:

$$R=\sqrt{L^2+r_1^2-2L(r_1\cos\theta+r_2\sin\theta)} \quad (4)$$

[7] The charged particle irradiation apparatus according to [6], wherein the focusing magnet has a first coil pair and a second coil pair, wherein the first coil pair and the second coil pair are arranged so as to interpose a path of a charged particle beam and be aligned in the Y-axis direction, and wherein the first coil pair and the second coil pair are configured such that orientations of magnetic fields of generated effective magnetic field regions are opposite to each other.

[8] The charged particle irradiation apparatus according to [6] or [7] further including a bending magnet that deflects a charged particle beam from an accelerator, which generates a charged particle beam, at a deflection angle $\phi$ that is larger than or equal to 10 degrees at the deflection point Q.

DESCRIPTION OF THE EMBODIMENTS

One embodiment of the present invention relates to a charged particle irradiation apparatus 10 including an irradiation nozzle that continuously moves along the shape on the exit side of an effective magnetic field region of a focusing magnet and irradiates an isocenter with a charged particle beam (also referred to as a particle ray) and a power supply system that supplies power to the irradiation nozzle.

Charged Particle Irradiation Apparatus 10

Figure 1:
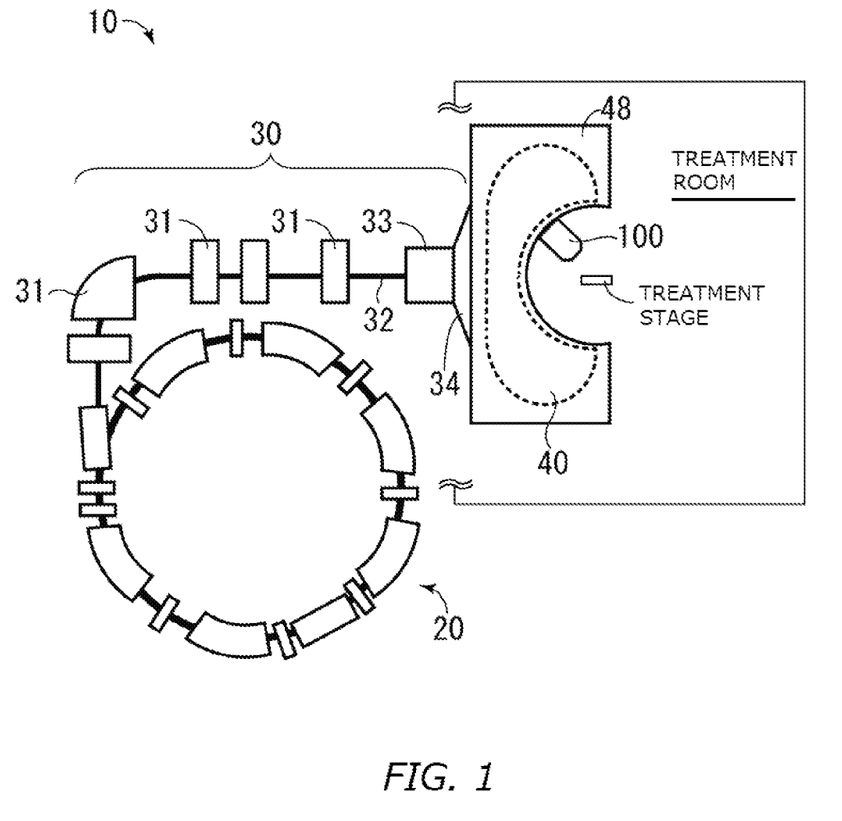
FIG. 1 is a schematic diagram of a configuration of a charged particle irradiation apparatus according to one embodiment of the present invention.

FIG. 1 is a schematic diagram of a configuration of the charged particle irradiation apparatus 10 according to one embodiment of the present invention. The charged particle irradiation apparatus 10 has a focusing magnet 40 and an irradiation nozzle 100. The charged particle irradiation apparatus 10 may further have an accelerator 20 and a charged particle beam transport system 30. The irradiation nozzle 100 is arranged inside a treatment room provided with a treatment stage on which a patient is placed.

The focusing magnet 40 is enclosed in a vacuum container, and the effective magnetic field region of the focusing magnet 40 through which a charged particle beam passes is maintained in a vacuum. The vacuum container (and a guide rail and a power supply rail described later) of the focusing magnet 40 is enclosed in a port cover 48, and the focusing magnet 40 and the power supply system 120 described later are unable to be seen from a patient or medical staff when the charged particle irradiation apparatus 10 is used. Accordingly, mental pressure or burden of a patient under particle therapy treatment is reduced, an accident such as an electric shock due to contact with a power supply rail described later is prevented, and safety is thus ensured. Note that the whole or a part of the irradiation nozzle 100 described later is located outside the port cover 48 and at a position seen from a patient under particle therapy treatment.

The accelerator 20 is an apparatus that generates a charged particle beam and may be, for example, a synchrotron, a cyclotron, or a linear accelerator. A charged particle beam generated by the accelerator 20 is guided to the focusing magnet 40 via the charged particle beam transport system 30.

The charged particle beam transport system 30 includes one or a plurality of charged particle beam adjustment units 31, a vacuum chamber 32, a bending magnet 33, a sector-shaped vacuum chamber 34, and the like. The accelerator 20, the charged particle beam adjustment units 31, and the bending magnet 33 are connected via the vacuum chambers 32, and the bending magnet 33 and the focusing magnet 40 are connected via the sector-shaped vacuum chamber 34. With the sector-shaped vacuum chamber 34 on the XY plane (see FIG. 2A) being shaped in a sector, a charged particle beam even deflected at a deflection angle $\phi$ that is larger than or equal to 10 degrees is able to pass inside the vacuum chamber, and this enables a reduction in the size and a reduction in the installation space compared to a rectangular vacuum chamber.

A charged particle beam is generated by the accelerator 20 on the upstream side, travels inside the vacuum chambers 32 and 34 to avoid or reduce attenuation, and is guided to the focusing magnet 40 on the downstream side while being adjusted by the charged particle beam adjustment unit 31.

The charged particle beam adjustment unit 31 includes a beam slit used for adjusting the beam shape and/or the dose of a charged particle beam, an electromagnet used for adjusting the beam direction of the charged particle beam, a quadrupole magnet used for adjusting the beam shape of the charged particle beam, a steering magnet used for finely adjusting the beam position of the charged particle beam, and the like if necessary in accordance with the specification.

The path from the bending magnet 33 for a charged particle beam to the isocenter O (an affected part of a patient) differs in accordance with the irradiation angle θ described later. Because of this, an optical element to which a charged particle beam is subjected may also change in accordance with the irradiation angle θ, and the beam shape of the charged particle beam at the isocenter O may change in accordance with the irradiation angle θ. To cope with this, for example, the charged particle beam adjustment unit 31 provided on the upstream side of the focusing magnet 40 may be controlled on an irradiation angle θ basis to perform adjustment so as to have a suitable beam shape of the charged particle beam at the isocenter O.

The bending magnet 33 is configured to continuously deflect a charged particle beam at the deflection angle φ described later and launch the charged particle beam to the focusing magnet 40. The focusing magnet 40 is configured to continuously change the irradiation angle θ of a charged particle beam traveling to the isocenter O. While the contents of prior patents (Japanese Patent No. 6364141 and Japanese Patent No. 6387476) owned by the same applicant as the present application are incorporated in the present specification by reference, examples of the bending magnet 33 and the focusing magnet 40 will now be briefly described below.

Figure 2A:
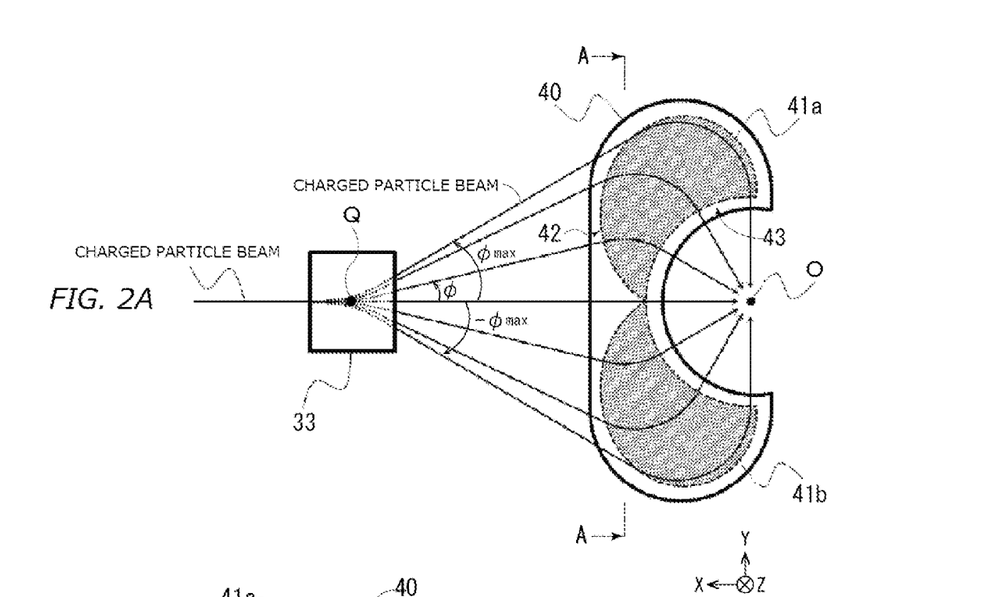
FIG. 2A and FIG. 2B are schematic diagrams of a configuration of a focusing magnet.
Figure 2B:
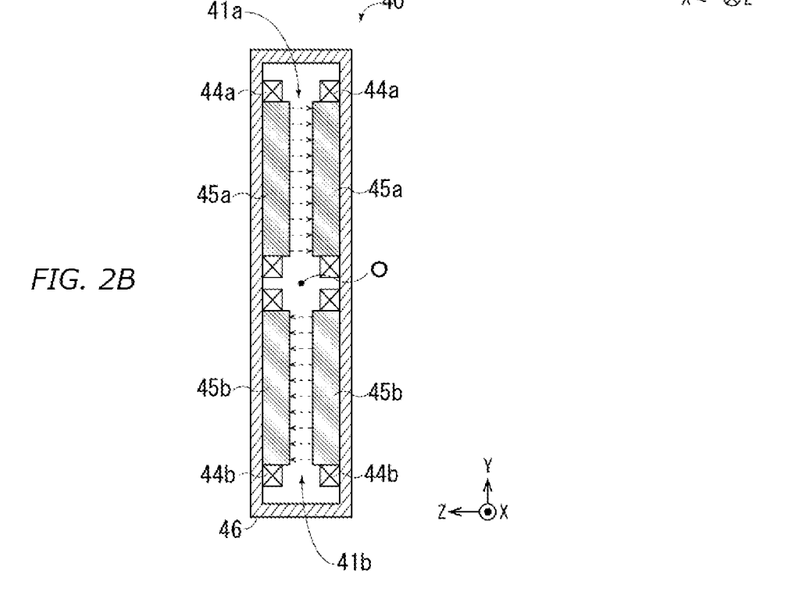

FIG. 2A is a schematic diagram of a configuration of the focusing magnet 40. In FIG. 2, the beam direction of a charged particle beam is defined as the X-axis, the direction of a magnetic field generated by the focusing magnet 40 is defined as the Z-axis, and the direction orthogonal to the X-axis and the Z-axis is defined as the Y-axis. The focusing magnet 40 is configured to converge a charged particle beam, which is incident from a wide range of the deflection angle φ relative to the X-axis, to the isocenter O on the XY plane. Note that, in FIG. 2A to FIG. 3, the irradiation nozzle 100 is omitted, and for simplified illustration, the isocenter O is defined as the origin of the XYZ space, and the upstream side (accelerator side) is defined as the positive direction of the X-axis.

The range of the deflection angle φ is a range larger than −90 degrees and smaller than +90 degrees, and a deflection angle range on the positive side (+Y-axis direction) and a deflection angle range on the negative side (−Y-axis direction) may be different from each other (asymmetry). For example, the positive side maximum deflection angle (φ=φmax) may be any one of 10 degrees, 15 degrees, 20 degrees, 25 degrees, 30 degrees, 35 degrees, 40 degrees, 45 degrees, 50 degrees, 60 degrees, 70 degrees, 80 degrees, and 85 degrees, and the negative side maximum deflection angle (φ=−φmax) may be any one of −10 degrees, −15 degrees, −20 degrees, −25 degrees, −30 degrees, −35 degrees, −40 degrees, −45 degrees, −50 degrees, −60 degrees, −70 degrees, −80 degrees, and −85 degrees.

The focusing magnet 40 has one or more sets of coil pairs, and each of the coil pairs generates an even magnetic field (effective magnetic field regions 41a and 41b) oriented in a direction (Z-axis direction in FIG. 2A) orthogonal to both the traveling direction of a charged particle beam and the spread direction of the deflection angle φ of the charged particle beam and is arranged so as to interpose the path of a charged particle beam. An effective magnetic field region generated by a set of coil pair of the focusing magnet 40 has a crescent-like shape on the XY plane as illustrated in FIG. 2A, and the details thereof will be described later. Note that, since the gap between paired facing coils (the distance in the Z-axis direction) through which a charged particle beam passes is sufficiently smaller than a range on the XY plane in which a charged particle beam spreads, the spread in the Z-axis direction of the charged particle beam is not taken into consideration here.

FIG. 2B is a sectional view taken along a line A-A of the focusing magnet 40. The focusing magnet 40 is preferably has at least two sets of coil pairs 44a and 44b. Magnetic poles (poles) 45a and 45b are embedded inside the coils 44a and 44b, respectively, and a yoke 46 is connected to the magnetic poles 45a and 45b. A power supply device (a magnet control unit 142 described later) is connected to the focusing magnet 40, current (excitation current) is supplied to the coil pairs 44a and 44b from the power supply device, thereby the focusing magnet 40 is excited, and the effective magnetic field regions 41a and 41b (that may be collectively referred to as an effective magnetic field region 41) are formed.

Note that the range of the effective magnetic field region 41a and the range of the effective magnetic field region 41b may be different from each other (asymmetry). For example, when the range of the deflection angle φ in the positive (the +Y-axis direction) and the range of the deflection angle φ in the negative (the −Y-axis direction) are asymmetric, by forming the effective magnetic field regions 41a and 41b to be asymmetric accordingly, it is possible to reduce the effective magnetic field region which is not used and reduce manufacturing cost or power consumption.

The range of the deflection angle φ of a charged particle beam deflected by the bending magnet 33 and entering the focusing magnet 40 ranges from the positive maximum deflection angle (φ=φmax) to the negative maximum deflection angle (φ=−φmax), the positive maximum deflection angle φmax is an angle that is larger than or equal to 10 degrees and smaller than 90 degrees, and the negative maximum deflection angle −φmax is an angle that is larger than −90 degrees and smaller than or equal to −10 degrees. The deflection angle φ and the irradiation angle θ described later are angles of the path of a charged particle beam relative to the X-axis on the XY plane.

A charged particle beam incident at the positive deflection angle range (0<φ≤φmax) is deflected by the effective magnetic field region 41a of the first coil pair 44a, passes through the irradiation nozzle 100, and is emitted to the isocenter O. A charged particle beam incident at the negative deflection angle range (−φmax≤φ<0) is deflected by the effective magnetic field region 41b of the second coil pair 44b, passes through the irradiation nozzle 100, and is emitted to the isocenter O. The magnetic fields of the effective magnetic field region 41a and the effective magnetic field region 41b are oriented in the opposite directions to each other. Note that the charged particle beam entering the focusing magnet 40 at the deflection angle φ=0 from the bending magnet 33 passes in either the effective magnetic field region 41a or 41b or between the effective magnetic field regions 41a and 41b and converges to the isocenter O through the irradiation nozzle 100.

The deflection angle φ of a charged particle beam entering the focusing magnet 40 is controlled by the bending magnet 33. The bending magnet 33 has an electromagnet that generates a magnetic field facing the direction (the Z-axis in the drawings) orthogonal to the beam direction (the X-axis in the drawings) of a charged particle beam supplied from an accelerator (not illustrated) and deflects the passing charged particle beam and a control unit (not illustrated) that controls the intensity and the orientation of the generated magnetic field. The bending magnet 33 deflects a charged particle beam on the XY plane and launches the charged particle beam deflected at the deflection angle φ at the deflection point Q to the focusing magnet 40 when a magnet control unit 142 described later controls the intensity and the orientation (the Z-axis direction) of the magnetic field of the bending magnet 33. Herein, the deflection point Q and the isocenter O are on the X-axis.

Figure 3:
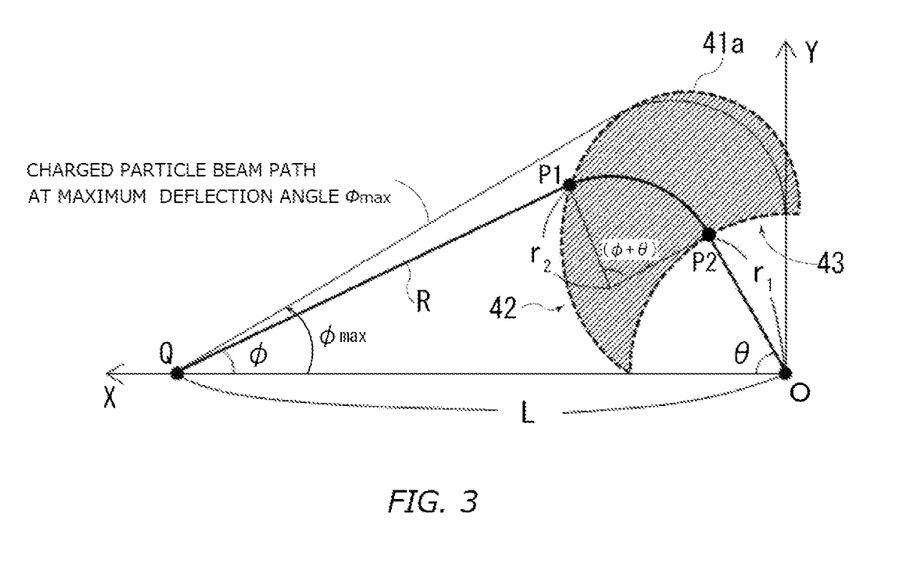
FIG. 3 is a diagram illustrating formation of an effective magnetic field region.

Calculation equations for forming the effective magnetic field region 41a of the focusing magnet 40 will be described with reference to FIG. 3. Note that, in the present embodiment, since deflection of a charged particle beam to the Z-axis direction is not taken into consideration, formation of effective magnetic field regions on the XY plane will be described. Although the effective magnetic field region 41a of the focusing magnet 40 will be described, since the same applies to the effective magnetic field region 41b, the description thereof will be omitted.

First, the boundary of the effective magnetic field region 41a on the exit side 43 of a charged particle beam of the focusing magnet 40 is determined so that the boundary is in a range located at an equal distance $r_1$ from the isocenter O. Next, the boundary of the effective magnetic field region 41a on the incident side 42 of the charged particle beam of the focusing magnet 40 is determined based on relational Equations (1) to (5) described later such that a charged particle beam deflected by the deflection angle φ and entering the virtual deflection point Q located at a predetermined distance L from the isocenter O converges to the isocenter O. Herein, the virtual deflection point Q is a point under the assumption that a charged particle beam is subjected to kick of the deflection angle φ within an extremely short distance at the center of the bending magnet 33.

A charged particle beam transported at the deflection angle φ enters an arbitrary (any) point P1 on the boundary of the effective magnetic field region 41a on the incident side 42, travels in circular movement with a radius of curvature $r_2$ within the effective magnetic field region 41a (the central angle at this time is (φ+θ)), exits a point P2 on the boundary of the effective magnetic field region 41a on the exit side 43, and is emitted to the isocenter O. That is, the point P1 and the point P2 are on an arc of a circle of the radius $r_2$ and the central angle (φ+θ).

The XY coordinate system having the isocenter O as the origin on the XY plane is considered. When the angle of a straight line connecting the point P2 on the exit side 43 to the isocenter O relative to the X-axis is defined as the irradiation angle θ, the coordinates (x, y) of the point P1 on the incident side 42, the deflection angle φ, and a distance R between point Q and the point P1 are found from the following relational Equations (1) to (4).

$$x = r_1\cos\theta + r_2(\sin\theta + \sin\phi) \quad (1)$$

$$y = r_1\sin\theta - r_2(\cos\theta - \cos\phi) \quad (2)$$

$$\phi = \sin^{-1}\left(\frac{r_2}{\sqrt{R^2 + r_2^2}}\right) + \sin^{-1}\left(\frac{r_1\sin\theta - r_2\cos\theta}{\sqrt{R^2 + r_2^2}}\right) \quad (3)$$

$$R = \sqrt{L^2 + r_1^2 - 2L(r_1\cos\theta + r_2\sin\theta)} \quad (4)$$

Herein, a magnetic field of an even magnetic flux density B occurs within the effective magnetic field region 41a, and the radius of curvature $r_2$ of a charged particle beam deflected in the magnetic field is expressed by Equation (5), where the momentum of a charged particle beam is denoted as p (substantially depending on an accelerator) and the charge is denoted as q.

$$r_2 = \frac{p}{qB} \quad (5)$$

It is possible to adjust the shape of the boundary of the effective magnetic field region 41a by adjusting the shape and the arrangement of the coil pairs 44a and the magnetic pole 45a of the focusing magnet 40 and adjusting current flowing in the coil pair 44a based on relational Equations (1) to (5) described above. That is, the boundary is defined such that the distance between the arbitrary point P2 on the boundary of the effective magnetic field region 41a on the exit side 43 and the isocenter O is the equal distance $r_1$, the magnetic flux density B of the effective magnetic field region 41a is adjusted to determine $r_2$ from Equation (5), and the boundary of the effective magnetic field region 41a on the incident side 42 is defined such that the distance R between the point P1 on the boundary of the effective magnetic field region 41a on the incident side 42 and the deflection point Q has the relationship of Equation (4). The local maximum value of φ in Equation (3) is the maximum deflection angle φmax. Note that, although not limited thereto, it is preferable that the arrangement of the deflection point Q, the focusing magnet 40, and the isocenter O be adjusted in advance so that a charged particle beam passing through the deflection point Q converges to the isocenter O without being subjected to deflection by the focusing magnet 40, because this can more simplify the configuration of the apparatus.

The boundary of the effective magnetic field regions 41a and 41b of the focusing magnet 40 found as described above is an ideal shape for converging a charged particle beam to the isocenter O. Note that, in the actual implementation, even when there is a shift from such an ideal shape or unevenness of a magnetic field distribution, it is possible to deflect a charged particle beam in accordance with the isocenter O by finely adjusting the excitation amount (magnetic flux density B) of the focusing magnet 40 on a deflection angle φ basis in advance, storing the information thereon in a power supply device (for example, the irradiation control unit 121), and controlling the deflection angle φ and the current amount of the focusing magnet 40 so that the deflection angle φ and the current amount are linked. Further, when unevenness of a magnetic field distribution can be predicted in advance, it is also possible to finely adjust the orbit of a charged particle beam by correcting the shape and the arrangement of the coil pairs 44a and 44b and the magnetic poles 45a and 45b of the focusing magnet 40.

Irradiation Nozzle 100

The irradiation nozzle 100 of the charged particle irradiation apparatus 10 will be described.

Figure 4:
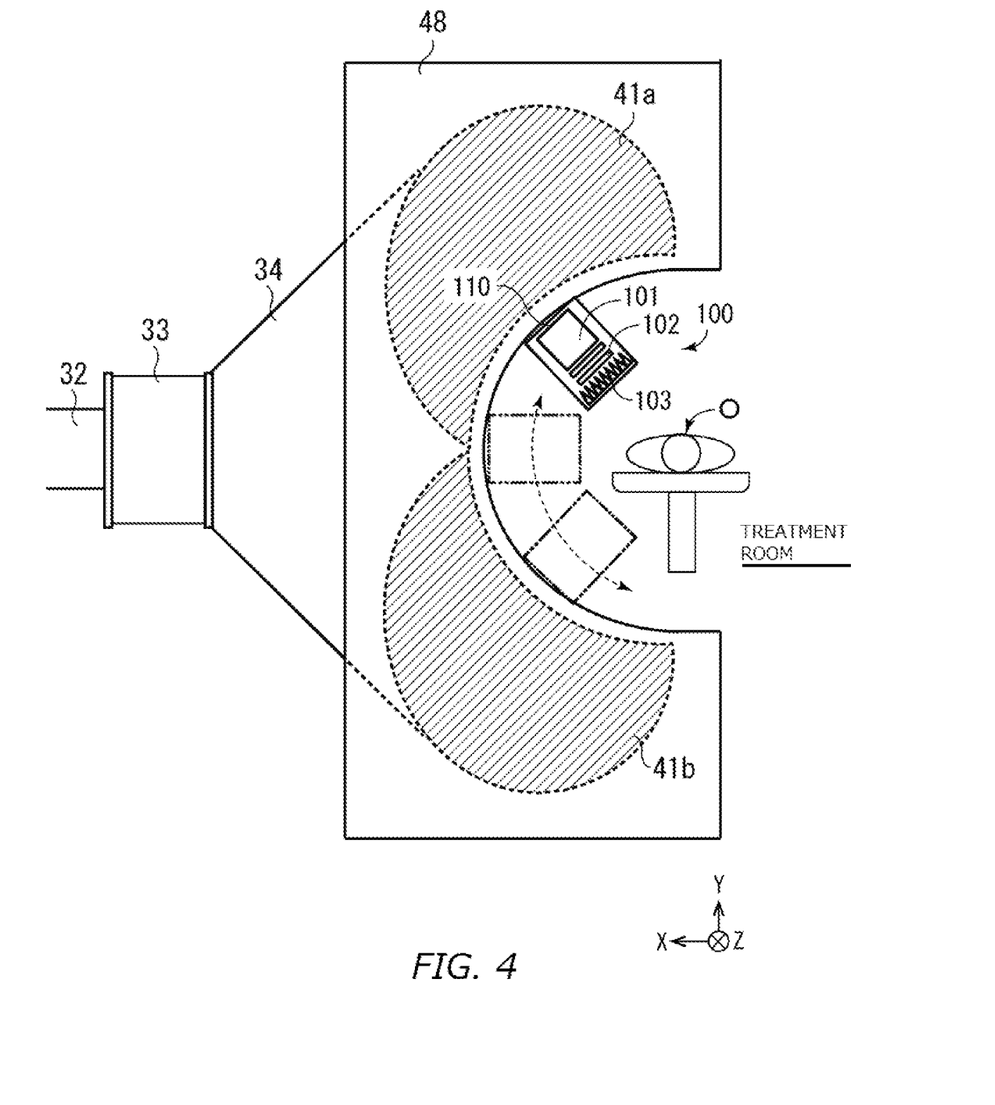
FIG. 4 is a schematic diagram of a configuration of the charged particle irradiation apparatus.

FIG. 4 is a schematic enlarged view of the downstream side of the charged particle irradiation apparatus 10, that is, the bending magnet 33, the sector-shaped vacuum chamber 34, the effective magnetic field region 41 (41a, 41b) of the focusing magnet 40, and the irradiation nozzle 100.

The irradiation nozzle 100 is located inside a treatment room in which treatment using a charged particle beam or the like are performed and continuously moves along the shape on the exit side 43 (boundary shape) of an effective magnetic field region 41 on the XY plane. The charged particle beam traveling from the exit side 43 of the effective magnetic field region 41 to the isocenter O passes inside the irradiation nozzle 100, and the beam traveling direction or the like of the charged particle beam are finely adjusted by the irradiation nozzle 100.

The irradiation nozzle 100 has a scanning magnet 101, a beam monitor 102, and an energy modulation unit 103. The scanning magnet 101 adjusts the amount of flowing current or the direction of current, thereby, finely adjusts the beam traveling direction of a charged particle beam launched from the irradiation nozzle 100, and enables a scan of a charged particle beam within a relatively narrow range. The beam monitor 102 monitors a charged particle beam and measures the position of a dose monitor or a beam and the flatness thereof. The energy modulation unit 103 adjusts the energy of a charged particle beam to adjust the depth in a patient reached by the charged particle beam. The energy modulation unit 103 is, for example, a range modulator, a scattering object, a ridge filter, a patient collimator, a patient bolus, an applicator, or a combination thereof.

Power Supply System 120

The power supply system 120 to the irradiation nozzle 100 will be described with reference to FIG. 5A to FIG. 9.

Figure 5A:
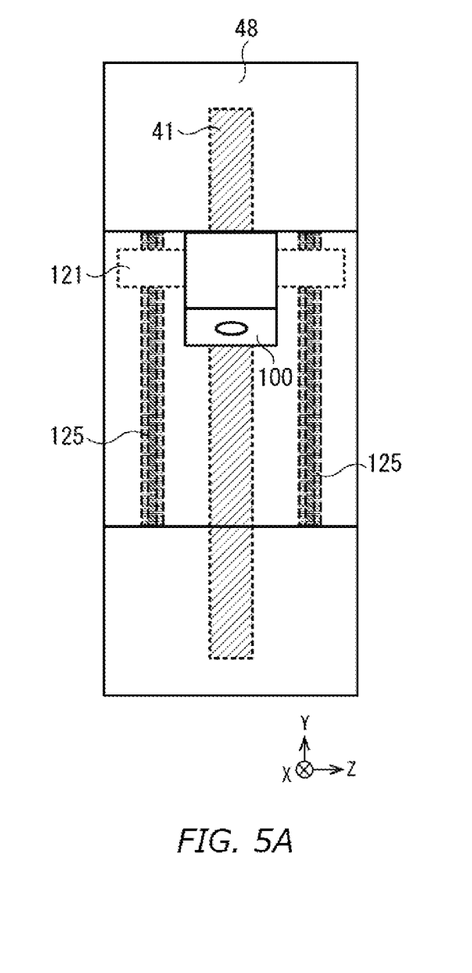
FIG. 5A and FIG. 5B are a front view and a side view of the irradiation nozzle side of the charged particle irradiation apparatus.
Figure 5B:
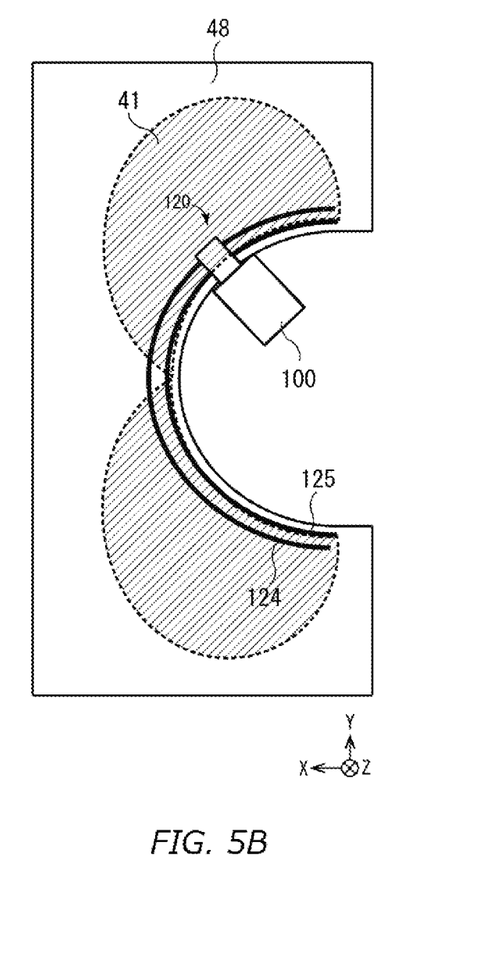
Figure 6A:
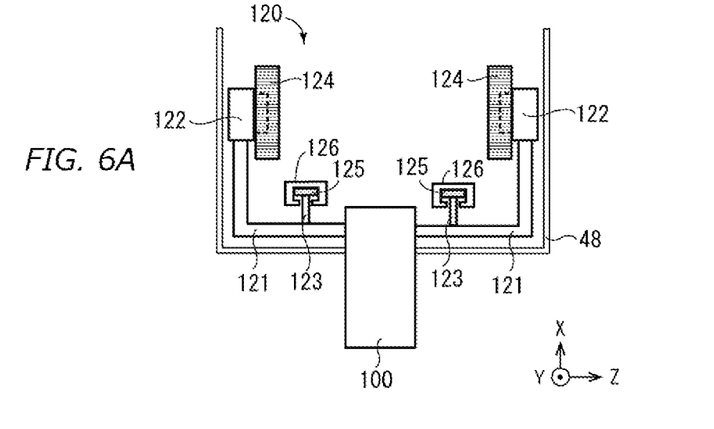
FIG. 6A to FIG. 6C are schematic sectional views of a configuration of the irradiation nozzle and a power supply system.
Figure 6B:
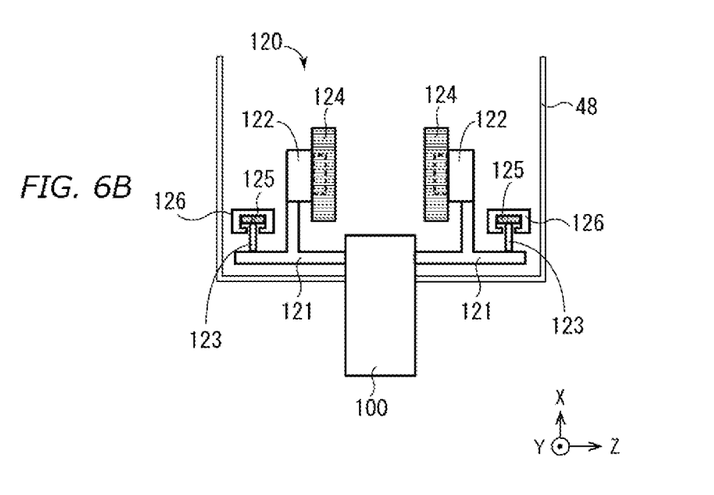
Figure 6C:
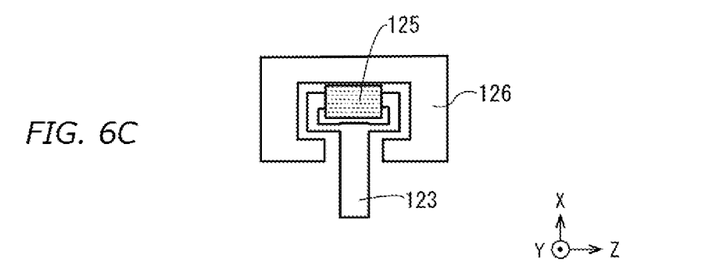

FIG. 5A is a front view of the charged particle irradiation apparatus 10 when viewed from a patient side, and FIG. 5B is a side view thereof. FIG. 6A to FIG. 6C are schematic diagrams of cross sections of the power supply system 120, the irradiation nozzle 100, and the port cover 48 when viewed from the top.

The power supply system 120 includes drive units 122 and collector shoes 123 provided to support members 121 fixed to the irradiation nozzle 100, guide rails 124 used for causing the irradiation nozzle 100 to move along the shape of the exit side 43 of the effective magnetic field region 41 of the focusing magnet 40, and power supply rails 125 used for supplying power to the irradiation nozzle 100 and the drive unit 122 via the collector shoes 123.

The power supply rail 125 is fixed inside the port cover 48 via insulating members 126 in order to prevent short circuit or electric leakage. Further, the number of guide rails 124 and the number of power supply rails 125 are not limited to the numbers as depicted, and any numbers greater than or equal to one thereof may be provided.

In the power supply system 120, the guide rails 124 and the power supply rails 125 are provided so as to extend along the shape of the exit side 43 of the effective magnetic field region 41 of the focusing magnet 40 on the XY plane inside the port cover 48 in which a vacuum container enclosing the focusing magnet 40 is enclosed. As used herein, "so as to extend along the shape of the exit side 43 of the effective magnetic field region 41" means that, while the guide rail 124 and the power supply rail 125 are at least configured such that a charged particle beam traveling from the exit side 43 of the effective magnetic field region 41 to the isocenter O can pass through inside the irradiation nozzle 100 for all the irradiation angles θ used in the charged particle irradiation apparatus 10, the guide rail 124 and the power supply rail 125 are preferably formed to be the same as or similar to the shape of the exit side 43 of the effective magnetic field region 41 on the XY plane. With the power supply rail 125 being formed to be the same or similar to the shape of the exit side 43 of the effective magnetic field region 41 on the XY plane, the change in a contact resistance between the collector shoe 123 and the power supply rail 125 can be suppressed even when the irradiation nozzle 100 is located anywhere within the guide range, and this is preferable in that a stable power supply can be obtained.

FIG. 6A represents a form in which the power supply rails 125 are located inside the guide rails 124, and FIG. 6B represents a form in which the guide rails 124 are located inside the power supply rails 125. While the present invention may take any form, since the relatively heavy irradiation nozzle 100 is located near the drive unit 122 in the form illustrated in FIG. 6B, influence of the moment applied to the support member 121 due to motion of the irradiation nozzle 100 can be reduced.

Note that, although the cross section of the power supply rail 125 is flat in the XZ plane in FIG. 6A to FIG. 6C, the cross section may be curved to the collector shoe 123 side in order to improve contact to the collector shoe 123. Further, as illustrated in FIG. 6C, the collector shoe 123 may be formed to pinch the flat side surface of the power supply rail 125. With such a configuration, the collector shoe 123 can slide along the power supply rail 125 while the contact between the flat surface of the collector shoe 123 and the flat side surface of the power supply rail 125 is highly maintained.

The drive unit 122 is fixed to the irradiation nozzle 100 via the support member 121 and has a drive motor and a drive mechanism configured to cause the irradiation nozzle 100 to continuously move along the guide rail 124 while being supported by the guide rail 124.

The charged particle beam exiting the exit side 43 of the effective magnetic field region 41 of the focusing magnet 40 travels linearly. Thus, the irradiation nozzle 100 is preferably configured such that the charged particle beam exiting the effective magnetic field region 41 is caused to enter the incident end (center position) of the irradiation nozzle 100, thereby the attenuation of the charged particle beam is most suppressed, and adjustment of the charged particle beam inside the irradiation nozzle 100 is facilitated. Further, by causing the irradiation nozzle 100 to move along the shape of the exit side 43 of the effective magnetic field region 41 on the XY plane, it becomes easier for the charged particle beam exiting the effective magnetic field region 41 to enter the incident end of the irradiation nozzle 100, and it is possible to avoid or reduce attenuation of the charged particle beam.

Each collector shoe 123 is fixed to the irradiation nozzle 100 via the support member 121, slides along the power supply rail 125 (can move while being in contact with the power supply rail 125), and supplies power from the power supply rail 125 to the irradiation nozzle 100 or the drive unit 122. Regardless of whether the irradiation nozzle 100 is moving or stopped, the collector shoe 123 can stably receive power supply from the power supply rail 125. The power supplied from the power supply rail 125 to the collector shoe 123 is used for the operation of the scanning magnet 101, the beam monitor 102, and the energy modulation unit 103 of the irradiation nozzle 100 or the operation of the drive unit 122.

Figure 7A:
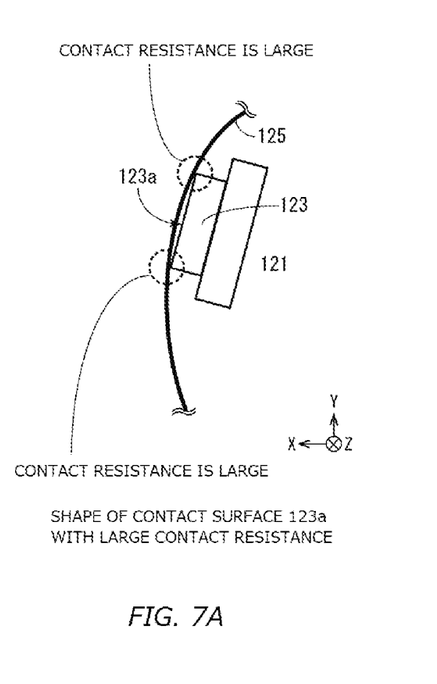
FIG. 7A and FIG. 7B are diagrams illustrating the shape of a contact surface of a collector shoe.
Figure 7B:
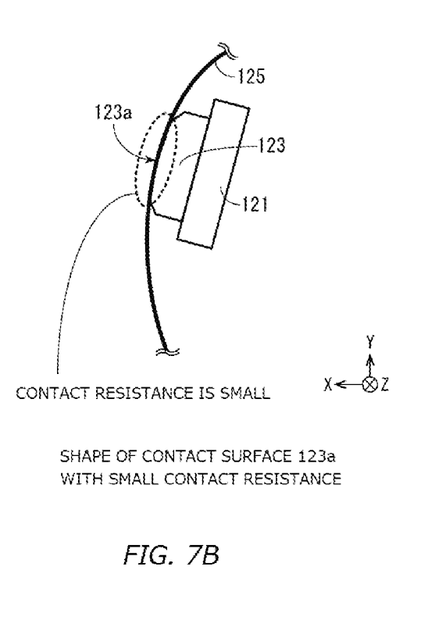

Herein, as illustrated in FIG. 7A and FIG. 7B, a contact surface 123a of the collector shoe 123 in contact with the power supply rail 125 is preferably formed to have the same radius as the bend radius of the power supply rail 125 on the XY plane (and/or the XZ plane and/or the YZ plane) (in the present invention, "the same" includes a case of being different within ±10%) or have an average bend radius of the power supply rail 125. For example, when the power supply rail 125 has the same bend radius in any portion within the guide range of the irradiation nozzle 100 on the XY plane, the contact surface 123a of the collector shoe 123 is preferably formed to have the same bend radius as the bend radius of the power supply rail 125. The contact resistance is relatively larger in a portion where the contact area between the collector shoe 123 and the power supply rail 125 is smaller (for example, a contact point), and associated heat generation is likely to occur. However, by forming the contact surface 123a of the collector shoe 123 to have the same bend radius as the bend radius of the power supply rail 125, it is possible to cancel or reduce the influence of heat generation due to the contact resistance.

Note that biasing means (not illustrated) that can apply a constant weight onto the collector shoe 123 may be provided between the collector shoe 123 and the support member 121. For example, the biasing means may preferably have two-layered structure of a plate spring and a coil spring so that a constant weight is applied onto the collector shoe 123 sliding on the power supply rail 125 in response to motion of the irradiation nozzle 100. Further, the biasing means that reduce interference between the power supply rail 125 and the collector shoe 123 may be provided on the power supply rail 125 side (for example, between the insulating member 126 and a fixing member of the port cover 48) instead of on the collector shoe 123 may be configured to bias the power supply rail 125 on the collector shoe 123 side with a constant weight and apply a constant weight onto the collector shoe 123 sliding on the power supply rail 125. As used herein, a constant weight means that a weight is applied to a degree that power supply from the power supply rail 125 to the collector shoe 123 is stably performed without being limited to a case where the same weight is always applied.

Figure 8:
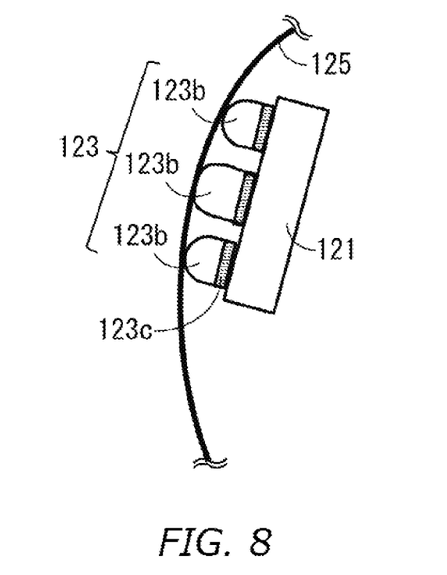
FIG. 8 is a diagram illustrating the shape of a plurality of collector portions of the collector shoe.

Further, as illustrated in FIG. 8, the collector shoe 123 may be formed of a plurality of collector portions 123b. In this case, biasing means 123c may be provided between each collector portion 123b and the support member 121. Accordingly, even when the bend radius of the power supply rail 125 is not completely even within the guide range of the irradiation nozzle 100, the collector shoe 123 can be stably in contact with the power supply rail 125 so as to extend flexibly along the shape of the power supply rail 125. Furthermore, it is more preferable that the contact surface of each collector portion 123b in contact with the power supply rail 125 be formed to have the same bend radius as the power supply rail 125 (or have the average bend radius of the power supply rail 125).

Figure 9:
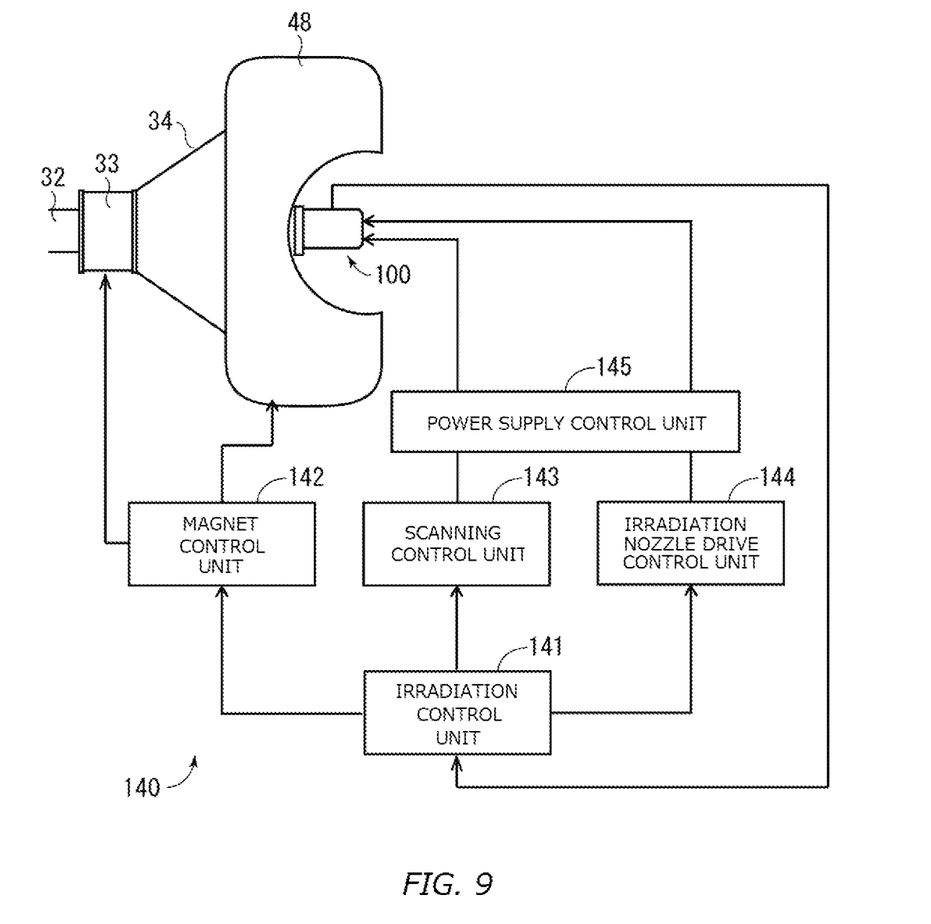
FIG. 9 is a block diagram of a control system of the charged particle irradiation apparatus.

FIG. 9 is a block diagram related to the control system 140 of the irradiation nozzle 100, the bending magnet 33, the focusing magnet 40, and the power supply system 120.

The control system 140 includes an irradiation control unit 141, a magnet control unit 142, a scanning control unit 143, an irradiation nozzle drive control unit 144, and a power supply control unit 145.

The irradiation control unit 141 is an upper level control unit that monitors a prescribed dose predefined for each target irradiated with a charged particle beam and controls the magnet control unit 142, the scanning control unit 143, and the irradiation nozzle drive control unit 144. The magnet control unit 142 controls the bending magnet 33 and the focusing magnet 40 to adjust the deflection angle φ (and the irradiation angle θ) of the charged particle beam. The scanning control unit 143 transmits, to the power supply control unit 145, an instruction used for controlling the scanning magnet 101 of the irradiation nozzle 100. The irradiation nozzle drive control unit 144 transmits, to the power supply control unit 145, an instruction used for controlling the drive unit 122 to control motion of the irradiation nozzle 100. The power supply control unit 145 controls power supply to the scanning magnet 101 and the drive unit 122 to operate the scanning magnet 101 and the drive unit 122 based on the instructions from the scanning control unit 143 and the irradiation nozzle drive control unit 144 on the upper level.

The irradiation control unit 141 transmits an instruction to the magnet control unit 142 and the irradiation nozzle drive control unit 144 in accordance with a predefined direction of a charged particle beam (irradiation angle θ) to be emitted to the isocenter O (affected part). The magnet control unit 142 that has received the instruction adjusts current to flow in the bending magnet 33 (and/or the focusing magnet 40) so that the irradiation angle θ of a charged particle beam exiting the focusing magnet 40 becomes a preset irradiation angle. Further, the irradiation nozzle drive control unit 144 that has received the instruction drives the drive unit 122 before starting irradiation of a charged particle beam and moves the irradiation nozzle 100 so that a charged particle beam exiting the focusing magnet 40 passes through the incident end (center) of the irradiation nozzle 100.

While irradiating an affected part with a charged particle beam, the irradiation control unit 141 may be configured to determine whether or not irradiation of the charged particle beam to the affected part is appropriate in response to information (information on the position and the width, the dose, or the like of a charged particle beam) from the beam monitor 102 of the irradiation nozzle 100 to perform feedback control. For example, if the direction of the charged particle beam (irradiation angle θ) is inappropriate compared to a direction preset for an affected part based on information from the beam monitor 102, the magnet control unit 142 (and/or the scanning control unit 143) is controlled to finely adjust the irradiation angle θ (and/or finely adjust the irradiation angle θ with scan by using the scanning magnet 101 of a charged particle beam within a predetermined range). Further, if the irradiation dose of the charged particle beam is inappropriate with respect to a value preset for an affected part, the irradiation dose of the charged particle beam emitted on the affected part may be adjusted by using the energy modulation unit 103 of the irradiation nozzle 100, the charged particle beam adjustment unit 31, and/or the like As described above, in the charged particle irradiation apparatus 10 according to the present embodiment, a relatively thick power supply cable for the irradiation nozzle 100 is not used, and power is supplied from the power supply rail 125 to the irradiation nozzle 100. Thus, there is no problem of a storage space of a thick cable having a large bend radius or damage on a cable due to handling. Further, the power supply rail 125 is provided inside the port cover 48 and thus is unable to be seen from a patient subjected to particle therapy treatment, and it is therefore possible to solve or reduce the problem of mental pressure, anxiety, or the like of the patient. Further, the shape of the contact surface 123a of the collector shoe 123 is formed to have the same bend radius as the bend radius of the power supply rail 125 (in the present invention, "the same" includes a case of being different within ±10%), thereby a contact resistance is reduced, the problem of heat generation can be solved or reduced, and this enables stable power supply. Further, the collector shoe 123 is formed of a plurality of collector portions 123b, and this enables stable power supply with continuous contact in a manner further fit to the shape of the power supply rail 125 even when the irradiation nozzle 100 moves. In this case, it is more preferable to provide the biasing means 123c between the collector shoe 123 (or each collector portion 123b) and the support member 121.

Since the charged particle irradiation apparatus according to one embodiment of the present invention is configured to supply power from a power supply rail to an irradiation nozzle without using a relatively thick power supply cable for operating the irradiation nozzle, the problem of a storage space of a thick cable having a large bend radius, the problem of damage on a cable due to handling of the cable, or the like can be solved or reduced.

The size, the material, the shape, the relative position of components, or the like described above may be changed in accordance with the structure of the apparatus to which the present invention is applied or various conditions. It is not intended to limit the disclosure to any specific terms used in the description and the embodiments, those skilled in the art can use another equivalent component, and the embodiments described above can be modified and changed differently as long as not departing from the spirit or the scope of the present invention. Further, even if not explicitly described, the feature described in association with one of the embodiments of the present invention can be used together with another embodiment.

The present application is based on and claims priority from Japanese Patent Application No. 2020-055716, filed Mar. 26, 2020, the disclosure of which is hereby incorporated by reference herein in its entirety.

LIST OF REFERENCE SYMBOLS 10 charged particle irradiation apparatus
20 accelerator
30 charged particle beam transport system
31 charged particle beam adjustment unit
32 vacuum chamber
33 bending magnet
34 sector-shaped vacuum chamber
40 focusing magnet
41 (41a, 41b) effective magnetic field region
42 incident side
43 exit side
44 (44a, 44b) coil
45 magnetic pole
46 yoke
48 port cover
100 irradiation nozzle
101 scanning magnet
102 beam monitor
103 energy modulation unit
120 power supply system
121 support member
122 drive unit
123 collector shoe
124 guide rail
125 power supply rail
126 insulating member
140 control system
141 irradiation control unit
142 magnet control unit
143 scanning control unit
144 irradiation nozzle drive control unit
145 power supply control unit

What is claimed is:

1. A charged particle irradiation apparatus comprising:
a focusing magnet that deflects a charged particle beam to continuously change an irradiation angle of the charged particle beam to an isocenter;
an irradiation nozzle that continuously moves along a shape on an exit side of an effective magnetic field region of the focusing magnet, wherein a charged particle beam exiting the focusing magnet is emitted to the isocenter through the irradiation nozzle;
a power supply rail provided so as to extend along the shape along the exit side of the effective magnetic field region; and
a collector shoe fixed to the irradiation nozzle via a support member and configured to slide on the power supply rail to supply power from the power supply rail to the irradiation nozzle,
wherein a surface of the collector shoe contacted with the power supply rail has the same bend radius as the power supply rail or an average bend radius of the power supply rail, and/or
wherein the collector shoe slides along the power supply rail while being in contact with a flat side surface of the power supply rail.

2. The charged particle irradiation apparatus according to claim 1, wherein while the focusing magnet, the power supply rail, and the collector shoe are enclosed in a port cover, a whole or a part of the irradiation nozzle is located outside the port cover.

3. The charged particle irradiation apparatus according to claim 1, wherein biasing means are provided between the support member and the collector shoe, and a constant weight is applied on the collector shoe by the biasing means.

4. The charged particle irradiation apparatus according to claim 1 further comprising:
a guide rail provided so as to extend along the shape on the exit side of the effective magnetic field region; and
a drive unit fixed to the irradiation nozzle via the support member and configured to continuously move along the guide rail while the irradiation nozzle is supported by the guide rail,
wherein power is supplied from the power supply rail to the drive unit via the collector shoe.

5. The charged particle irradiation apparatus according to claim 1,
wherein the focusing magnet has a coil pair arranged so as to interpose a path of a charged particle beam,
wherein the coil pair is configured to generate an effective magnetic field region whose magnetic field is oriented to a direction (Z-axis) orthogonal to a traveling direction (X-axis) of a charged particle beam in response to input of current, where an axis orthogonal to both the X-axis and the Z-axis is defined as a Y-axis,
wherein on the XY plane,
a charged particle beam deflected at a deflection angle φ relative to the X-axis at a deflection point Q and entering the effective magnetic field region is deflected by the effective magnetic field region and is emitted to the isocenter at an irradiation angle θ relative to the X-axis through the irradiation nozzle,
an arbitrary point P2 on a boundary defining the effective magnetic field region and located on an exit side of a charged particle beam is located at an equal distance $r_1$ from the isocenter, the point P2 and a point P1 on a boundary defining the effective magnetic field region and located on an incident side of a charged particle beam are on an arc of a circle of a radius $r_2$ and a central angle $(\theta+\phi)$, and a distance R between the deflection point Q and the point P1 satisfies relational Equation (4), where a distance between the deflection point Q and the isocenter is denoted as L:

$$R=\sqrt{L^2+r_1^2-2L(r_1\cos\theta+r_2\sin\theta)} \qquad (4).$$

6. The charged particle irradiation apparatus according to claim 5,
   wherein the focusing magnet has a first coil pair and a second coil pair,
   wherein the first coil pair and the second coil pair are arranged so as to interpose a path of a charged particle beam and be aligned in the Y-axis direction, and
   wherein the first coil pair and the second coil pair are configured such that orientations of magnetic fields of generated effective magnetic field regions are opposite to each other.

7. The charged particle irradiation apparatus according to claim 5 further comprising a bending magnet that deflects a charged particle beam from an accelerator, which generates a charged particle beam, at a deflection angle $\phi$ that is larger than or equal to 10 degrees at the deflection point Q.

8. A charged particle irradiation apparatus comprising:
   a focusing magnet that deflects a charged particle beam to continuously change an irradiation angle of the charged particle beam to an isocenter;
   an irradiation nozzle that continuously moves along a shape on an exit side of an effective magnetic field region of the focusing magnet, wherein a charged particle beam exiting the focusing magnet is emitted to the isocenter through the irradiation nozzle;
   a power supply rail provided so as to extend along the shape on the exit side of the effective magnetic field region; and
   a collector shoe fixed to the irradiation nozzle via a support member and configured to slide along the power supply rail to supply power from the power supply rail to the irradiation nozzle,
   wherein the collector shoe is formed of a plurality of collector portions, and
   wherein a surface of each of the collector portions that is contacted with the power supply rail has the same bend radius as the power supply rail or an average bend radius of the power supply rail.

* * * * *